United States Patent [19]

Wingen et al.

[11] Patent Number: 4,891,151
[45] Date of Patent: Jan. 2, 1990

[54] LIQUID-CRYSTALLINE PHENYLPYRIMIDINYL CYCLOHEXANECARBOXYLATES HAVING A SMECTIC PHASE, A PROCESS FOR THEIR PREPARATION, AND THEIR USE IN LIQUID-CRYSTAL MIXTURES

[75] Inventors: Rainer Wingen, Hattersheim am Main; Hans-Rolf Dübal, Königstein/Taunus; Claus Escher, Mühltal; Wolfgang Hemmerling, Sulzbach (Taunus); Ingrid Müller, Hofheim am Taunus; Dieter Ohlendorf, Liederbach, all of Fed. Rep. of Germany

[73] Assignee: Hoechst Aktiengesellschaft, Frankfurt am Main, Fed. Rep. of Germany

[21] Appl. No.: 245,452

[22] Filed: Sep. 16, 1988

[30] Foreign Application Priority Data

Sep. 19, 1987 [DE] Fed. Rep. of Germany ....... 3731639

[51] Int. Cl.⁴ .................. G02F 1/13; C09K 19/34; C07D 239/26; G09F 9/35
[52] U.S. Cl. .................. 252/299.61; 252/299.01; 350/350 R; 350/350 S; 544/248; 544/335
[58] Field of Search ............ 252/299.01, 299.61; 250/350 R, 350 S; 544/298, 335

[56] References Cited

U.S. PATENT DOCUMENTS

| | | | |
|---|---|---|---|
| 4,311,610 | 1/1982 | Zaschke et al. | 252/299.61 |
| 4,621,901 | 11/1986 | Petrzilka et al. | 252/299.61 |
| 4,744,918 | 5/1988 | Heppke et al. | 252/299.61 |
| 4,752,414 | 6/1988 | Eidenschink et al. | 252/299.61 |
| 4,776,973 | 10/1988 | Bofinger et al. | 252/299.61 |
| 4,820,839 | 4/1989 | Krause et al. | 252/299.61 |
| 4,834,904 | 5/1989 | Krause et al. | 252/299.61 |

FOREIGN PATENT DOCUMENTS

| | | | |
|---|---|---|---|
| 0025119 | 3/1981 | European Pat. Off. | 252/299.61 |
| 0151446 | 8/1985 | European Pat. Off. | 252/299.61 |
| 268198 | 5/1988 | European Pat. Off. | 252/299.61 |
| 3404117 | 8/1985 | Fed. Rep. of Germany | 252/299.61 |
| 3500909 | 7/1986 | Fed. Rep. of Germany | 252/299.61 |
| 3515373 | 11/1986 | Fed. Rep. of Germany | 252/299.61 |
| 3518734 | 11/1986 | Fed. Rep. of Germany | 252/299.61 |
| 260709 | 10/1988 | German Democratic Rep. | 252/299.61 |
| 61-215375 | 9/1986 | Japan | 252/299.61 |
| 8607055 | 12/1986 | World Int. Prop. O. | 252/299.61 |

OTHER PUBLICATIONS

Kelly, S. M. et al., Liq. Cryst., vol. 3(9), pp. 1173–1182 (Sep. 1988).

*Primary Examiner*—Teddy S. Gron
*Attorney, Agent, or Firm*—Curtis, Morris & Safford

[57] ABSTRACT

Liquid-crystalline phenylpyrimidinyl cyclohexanecarboxylates having a smectic phase, a process for their preparation, and their use in liquid-crystal mixtures The phenylpyrimidinyl trans-cyclohexanecarboxylates of the general formula

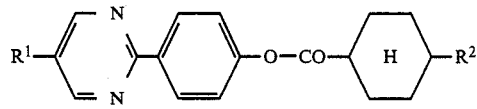

form a smectic C phase besides a relatively broad nematic phase when $R^1$ denotes an alkyl radical having 10 to 16 carbon atoms, in particular 11 to 16 carbon atoms, or an alkoxy radical having 8 to 14 carbon atoms, and $R^2$ denotes an alkyl radical having 2 to 9 carbon atoms. They are therefore particularly suitable as components of liquid-crystalline mixtures having a smectic C phase since they induce a relatively broad nematic phase or extend a narrow nematic phase which is present and extend the temperature range of the smectic C phase to low temperatures, but in particular to high temperatures.

5 Claims, No Drawings

LIQUID-CRYSTALLINE PHENYLPYRIMIDINYL CYCLOHEXANECARBOXYLATES HAVING A SMECTIC PHASE, A PROCESS FOR THEIR PREPARATION, AND THEIR USE IN LIQUID-CRYSTAL MIXTURES

Due to their favorable properties, such as short switching times, the possibility of bistable switching and the contrast which is virtually independent of the view angle, ferroelectric liquid crystals have recently aroused interest as display media for electrooptical components.

Ferroelectric liquid crystals may themselves by chiral compounds which form chiral smectic phases, in particular $S_c^*$ phases. However, ferroelectric liquid-crystal mixtures are also obtained by a process in which compounds or mixtures which do not themselves have a chiral structure, but form tilted smectic phases, are doped with chiral compounds [M. Brunet, Cl. Williams, Ann. Phys. 3, 237 (1978)].

For industrial use of liquid-crystal mixtures of this type, it is firstly necessary for the smectic phase, in particular the $S_c^*$ phase, to be stable over a broad temperature range. In order to achieve high contrast conditions in electrooptical components, it is furthermore necessary for the liquid crystals to have a uniform planar orientation. It is known that a uniform planar orientation can be achieved with the $S_c^*$ phase when the phase sequence of the liquid-crystal system is

with decreasing temperature (for example T. Matsumoto et al., Proc. of the 6th Int. Display Research Conf., Japan Display, Sept. 30–Oct. 2, 1986, Tokyo, pages 468–470; M. Murakami et al., loc. cit., pages 344–347). Liquid-crystalline compounds or systems having a broad $S_c$ phase frequently form only a very narrow nematic phase, or none at all. The addition of a compound having a broad nematic phase to $S_c$ compounds or systems of this type impairs the $S_c$ phase or causes it to disappear.

It has now been found that phenylpyrimidinyl trans-cyclohexanecarboxylates of the general formula (I)

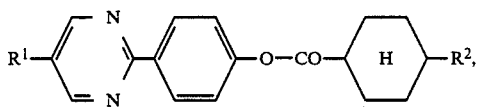

in which $R^1$ denotes an alkyl radical having 10 to 16 carbon atoms, in particular 11 to 16 carbon atoms, or an alkoxy radical having 8 to 14 carbon atoms, and $R^2$ denotes an alkyl radical having 2 to 9 carbon atoms, besides forming nematic phases which are sufficiently broad for practical purposes, also form smectic phases, in particular $S_c$ phase, with in some cases notably broad temperature ranges.

EP-A 0,025,119 discloses [4-(5-alkylpyrimidin-2-yl)]phenyl 4-alkylcyclohexanecarboxylates in which, in the specific examples, the alkyl substituents contain five or six carbon atoms. Furthermore, EP-A 0,151,446 and WO-A 86/07055 contain references to compounds of this type. In cases where specific compounds are indicated at all in these publications, they do not, however, have any smectic phase. The appearance of a smectic C phase besides a relatively broad nematic phase in the compounds according to the invention was therefore unexpected. Instead, it would have been expected that only a nematic phase occurs in this class of compounds.

The novel compounds according to the invention are thermally, chemically and photochemically stable. They are obtained from the underlying 4-(5-alkyl- or 5-alkoxypyrimidin-2-yl)phenols, or the alkali metal or alkaline earth metal salts thereof, through reaction with appropriate 4-alkyl-(trans)-cyclohexanecarboxylic acids or the halides thereof, in particular the chlorides.

In order to prepare the compounds (I), the phenols and the acid chlorides are preferably employed, the reaction being carried out in the presence of acid scavengers, such as amines, for example pyridine or triethylamine, or in the presence of alkaline earth metal or alkali metal (hydrogen) carbonates, in general at temperatures between −40° and +70° C. However, it is also possible to react the phenols with the acids in the presence of Brönstedt or Lewis acids, if appropriate in the presence of water-binding agents or with physical removal of the water of reaction, for example by azeotropic distillation or absorption, or with the aid of condensation reagents such as N,N′-carbonyldiimidazole, dicyclohexylcarbodiimide or azodicarboxylates/triphenylphosphine. It is also possible to react the alkali metal salts or alkaline earth metal salts of the phenols with the carbonyl halides, in particular the chlorides. The crude product obtained in each case can be purified in a manner known per se, for example by recrystallization or by column chromatography.

The compounds according to the invention are particularly highly suitable as components of smectic liquid-crystalline mixtures, since they have both nematic and smectic C phases. If the compounds according to the invention are added to mixtures of liquid crystals or even to individual liquid-crystalline compounds which have a $S_c$ and $S_A$ phase, but only have a very narrow nematic phase, or none at all, the novel compounds induce or extend the nematic phase desired and simultaneously extend the temperature range of the $S_c$ phase, even when added in small amounts, from about 4 mol-% in the mixture. It is particularly remarkable that not only does the $S_c$ phase frequently extend to low temperatures, but also the $S_c/S_A$ phase boundary is shifted to higher temperatures (Examples 10 to 13). It is of course also possible to mix the compounds according to the invention with one another in order to extend the $S_c$ phase, in particular to reduce the lower temperature limit compared with the starting compounds. For this reason, it is also possible to use optimized mixtures of the compounds according to the invention as components of ferroelectric/smectic C mixtures.

The invention therefore also relates to the use of the compounds according to the invention, individually or as mixtures with one another, as components of liquid-crystalline smectic C mixtures or liquid-crystalline ferro-electric mixtures in order to induce or extend a liquid-crystalline nematic phase, the temperature range of the smectic C phase usually not being reduced, but frequently extended to low temperatures and, in particular, to high temperatures.

It is furthermore advantageous for the use of the compounds according to the invention in ferroelectric liquid-crystalline mixtures that they have a negative dielectric anisotropy (cf. Example 14) and a very low optical anisotropy (cf. Example 15). The dielectric and optical properties of mixtures are positively effected thereby (cf. Lagerwall et al., "Ferroelectric Liquid Crystals for Displays", SID Symposium, Oct. Meeting 1985, San Diego, Ca. USA)

EXAMPLE 1

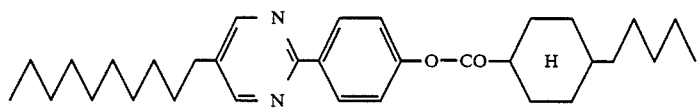

[4-(5-Decylpyrimidin-2-yl)]phenyl trans-4-pentylcyclohexanecarboxylate

A solution of 35.4 g of 4-(5-decylpyrimidin-2-yl)phenol, 22.5 g of trans-4-pentylcyclohexanecarboxylic acid and 23.4 g of N,N'-dicyclohexylcarbodiimide in 600 ml of dichloromethane is stirred at 20° C. for 12 hours. The N,N'-dicyclohexylurea formed is filtered off, and the filtrate is chromatographed over 5 kg of silica gel using dichloromethane. The product-containing fraction gives 21.5 g of colorless crystals after recrystallization from n-hexane.

Phase sequence C(10 $S_x$ 51.5) 62.8 $S_3$ 85.7 $S_c$ 104.5 N 162.4 I.

The following are obtained analogously:

EXAMPLE 2

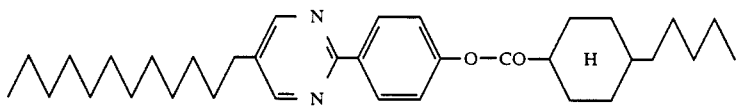

[4-(5-Undecylpyrimidin-2-yl)]phenyl trans-4-pentylcyclohexanecarboxylate

Phase sequence C 70 $S_x$ 80 $S_2$ 82.7 $S_c$ 114.5 N 160.5 I.

EXAMPLE 3

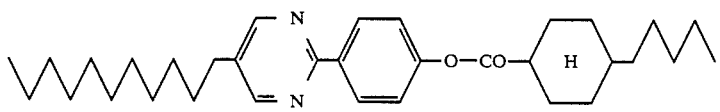

[4-(5-Dodecylpyrimidin-2-yl)]phenyl trans-4-pentylcyclohexanecarboxylate

Phase sequence C 67 $S_3$ 83 $S_2$ 87.2 $S_c$ 121 N 156 I.

EXAMPLE 4

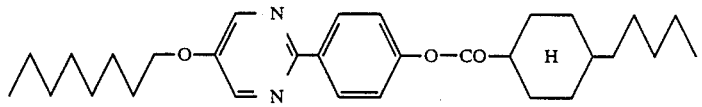

[4-(5-Octyloxypyrimidin-2-yl)]phenyl trans-4-pentylcyclohexancarboxylate

Phase sequence C (35 $S_x$ 68) 72.1 $S_3$ 74 $S_c$ 100 N 193 I.

EXAMPLE 5

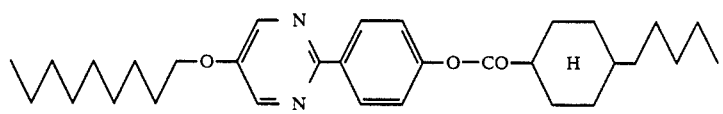

[4-(5-Nonyloxypyrimidin-2-yl)]phenyl trans-4-pentylcyclohexanecarboxylate

Phase sequence C ($C_2$ 64 $S_G$ 69) 74.3 $S_c$ 117.7 N 189 I.

EXAMPLE 6

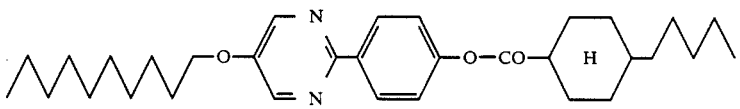

[4-(5-Decyloxypyrimidin-2-yl)]phenyl trans-4-pentylcyclohexanecarboxylate

Phase sequence C ($C_2$ 65 $S_G$ 72.5) 74.7 $S_c$ 129.8 N 186.5 I.

EXAMPLE 7

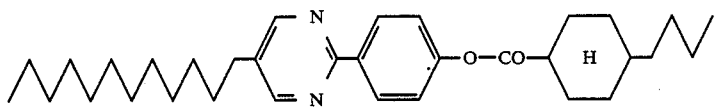

[4-(5-Dodecylpyrimidin-2-yl)]phenyl trans-4-butylcyclohexanecarboxylate

Phase sequence C 80 S$_3$ 82 S$_2$ 83.8 S$_c$ 115.3 N 152.7 I.

EXAMPLE 8

A binary mixture of 50 mol-% of each of the two compounds
[4-(5-octyloxypyrimidin-2-yl)]phenyl trans-4-pentylcyclohexanecarboxylate (Example 4) and
[4-(5-undecylpyrimidin-2-yl)]phenyl trans-4-pentylcyclohexanecarboxylate (Example 5)
exhibits a phase sequence of C 45 S$_2$ 70.7 S$_c$ 107.5 N 177.5 I.

USE EXAMPLES 9-12

Binary mixtures are produced in which one component is in each case a compound according to the invention and the other component is a compound having a S$_c$ phase, but which has only a very narrow nematic phase or none at all. The S$_c$-phase-containing components used are I: 5-decyl-2-(4-octyloxyphenyl)pyrimidine
II: 5-octyloxy-2-(4-octyloxyphenyl)pyrimidine
III: 5-nonyloxy-2-(4-heptyloxyphenyl)pyrimidine
IV: 4-(4-decyloxyphenyl-1-carbonyloxy)-1-(4-methylhexyloxy)benzene.

Table I collates the results. The phase sequences are given in each case for the pure compounds I to IV and for the binary mixtures.

The results in Table I clearly demonstrate the good mixing properties of the novel compounds. In all examples, starting from the compounds I to IV (compound A), the temperature range of the S$_c$ phase is extended and a nematic phase is induced or extended in the mixture A+B by adding only 15 mol-% of the compounds according to the invention (compound B).

(1) 5-octyloxy-2-(4-octyloxyphenyl)pyrimidine
(2) 5-octyloxy-2-(4-hexyloxyphenyl)pyrimidine: 59.5 mol-%
(3) 5-octyloxy-2-(4-butyloxyphenyl)pyrimidine
(4) 4-(4-decyloxyphenyl-1-carbonyloxy)-1-(4-methylhexyloxy)benzene: 30 mol-%
(5) [4-(5-decylpyrimidin-2-yl)]phenyl trans-4-pentylcyclohexanecarboxylate: 10.5 mol-%
exhibits the following phase behavior:
C-1 S$_c$ 74.5 S$_A$ 83.8 N 92.5 I
In this example too, the width of the nematic phase is extended from 0.8° C. to 8.7° C. by adding a compound according to the invention (component 5).

EXAMPLE 14

The dielectric constants are determined for the compound of Example 1. At 95° C. and a measurement frequency of 20 KHz, these are: $\epsilon\perp = -0.37$ and $\epsilon\|  = -1.23$, which means that a value of $-0.86$ is produced for the dielectric anisotropy $\Delta\epsilon$.

EXAMPLE 15

Using the two compounds from Example 1 and Example 4, mixtures are in each case produced with 50 mol-% of the compound V (4-(5-octylpyrimidin-2-yl)-1-(6-methyloctyloxy)benzene, and the optical anisotropy, $\Delta n$, is determined at 50° C. for the two mixtures and for the individual compound V:

Compound V: $\Delta n = 0.134$
Mixture with Example 1: $\Delta n = 0.108$
Mixture with Example 4: $\Delta n = 0.0974$
With linear extrapolation to the pure compounds, $\Delta n = 0.082$ for the compound from Example 1 and $\Delta n = 0.0608$ for the compound from Example 4.

EXAMPLE 16

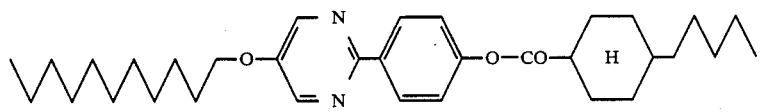

[4-(5-undecyloxypyrimidin-2-yl)]phenyl trans-4-pentylcyclohexanecarboxylate

Phase sequence C 80 S$_2$ 81 S$_c$ 136 N 181 I.

EXAMPLE 17

TABLE I

| Example | Compound A: Phase sequence* | Compound B (compound of Example ...) | Molar mixing ratio A/B | Phase sequence* |
|---|---|---|---|---|
| 9 | I: C 40.1 S$_c$ 69.1 S$_A$ 74.7 I | Example 6 | 85/15 | C 35 S$_c$ 78.6 S$_A$ 80.8 N 92 I |
| 10 | II: C 50.7 S$_c$ 92.3 S$_A$ 99.5 N 100.3 I | Example 6 | 85/15 | C 44 S$_c$ 96.5 S$_A$ 100 N 109.2 I |
| 11 | III: C 56 S$_c$ 94.4 S$_A$ 97.5 I | Example 4 | 85/15 | C 47 S$_c$ 98.6 S$_A$ 99.8 N 107 I |
| 12 | IV: C 45 S$_c$ 70.4 S$_A$ 73.3 I [17 S$_G$ 33 S$_c$] | Example 1 | 85/15 | C 27.3 S$_c$ 72.4 S$_A$ 74.6 N 81 I |

*The symbols have the following meanings:
C - crystalline, S$_c$ - smectic C, S$_A$ - smectic A, N - nematic, I - isotropic
the numerical values between the phase designations indicate the conversion temperatures in °C. in each case.

EXAMPLE 13

A mixture of the components

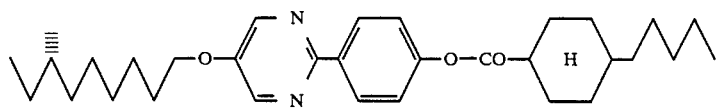

[4-<5-{(S)-7-Methylnonyloxy}pyrimidin-2-yl>]phenyl trans-4-pentylcyclohexanecarboxylate Phase sequence C 60 $S_2$ 84 $S_c$ 114 N 171 I.
$[\alpha]_D^{25}$: −3.75 (c=2, $CHCl_3$).

EXAMPLE 18

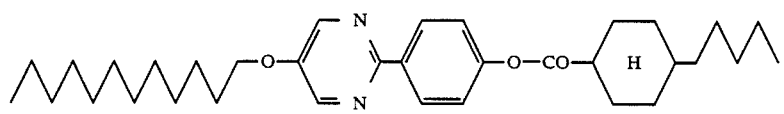

[4-(5-dodecyloxypyrimidin-2-yl)]phenyl trans-4-pentylcyclohexanecarboxylate

Phase sequence C 81 $S_2$ 90 $S_c$ 143 N 181 I.

EXAMPLE 19

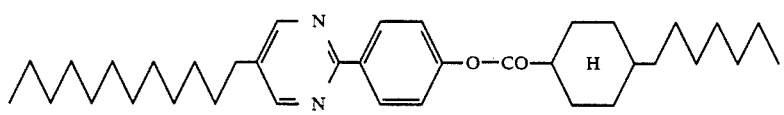

[4-(5-dodecylpyrimidin-2-yl)]phenyl trans-4-heptylcyclohexanecarboxylate

Phase sequence C 79.1 $S_2$ 87.2 $S_c$ 115 N 155.7 I.

We claim:

1. A phenylpyrimidinyl trans-cyclohexanecarboxylate of the formula (I)

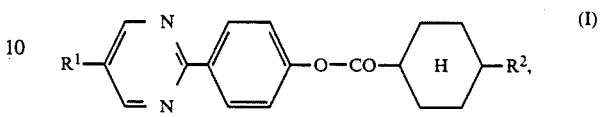

in which $R^1$ is an alkyl radical having 11 to 16 carbon atoms, or an alkoxy radical having 8 to 14 carbon atoms, and $R^2$ is an alkyl radical having 2 to 9 carbon atoms.

2. A liquid-crystalline mixture having at least one smectic phase, and containing at least one compound of the formula (I)

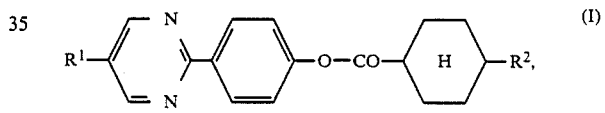

in which $R^1$ is an alkyl radical having 10 to 16 carbon atoms or an alkoxy radical having 8 to 14 carbon atoms, and $R^2$ is an alkyl radical having 2 to 9 carbon atoms.

3. A liquid-crystalline mixture as claimed in claim 2 having a $S_c$-phase.

4. A display medium for an electrooptical component, which medium contains a liquid-crystalline mixture as claimed in claim 2.

5. A display medium for an electrooptical component, which medium contains a liquid-crystalline mixture as claimed in claim 3.

* * * * *